United States Patent [19]

Maekawa

[11] Patent Number: 4,850,361
[45] Date of Patent: Jul. 25, 1989

[54] ULTRASONIC IMAGING APPARATUS

[75] Inventor: Hiromi Maekawa, Ootawara, Japan

[73] Assignee: Kabushiki Kaisha Toshiba, Kawasaki, Japan

[21] Appl. No.: 48,939

[22] Filed: May 12, 1987

[30] Foreign Application Priority Data

May 14, 1986 [JP] Japan ................................ 61-108565

[51] Int. Cl.$^4$ .............................................. A01B 8/00
[52] U.S. Cl. ................................ 128/660.04; 128/700
[58] Field of Search ............... 128/700, 715, 660, 661, 128/660.04, 661.09

[56] References Cited

U.S. PATENT DOCUMENTS

| | | | |
|---|---|---|---|
| 3,773,033 | 11/1973 | Rodbard et al. ................. | 128/700 X |
| 3,878,832 | 4/1975 | Tickner et al. .................. | 128/715 X |
| 4,094,308 | 6/1978 | Cormier ............................ | 128/715 |
| 4,159,462 | 6/1979 | Rocha et al. .................... | 128/661 X |
| 4,183,046 | 1/1980 | Dalke et al. ..................... | 358/22 |
| 4,398,540 | 8/1983 | Takemura et al. .............. | 128/660.05 |
| 4,462,872 | 5/1984 | Marsoner et al. ............... | 128/700 |
| 4,543,826 | 10/1985 | Ferrari ............................. | 73/602 |
| 4,573,477 | 3/1986 | Namekawa et al. ............ | 128/661.04 |
| 4,598,589 | 7/1986 | Riley et al. ....................... | 128/663 X |
| 4,622,977 | 11/1986 | Namehawa et al. ............ | 128/663 |
| 4,641,668 | 2/1987 | Namekawa ...................... | 128/661.09 |
| 4,660,565 | 4/1987 | Shirasaka ......................... | 128/661.09 |
| 4,677,634 | 11/1986 | Fidel ................................. | 128/660 X |
| 4,682,229 | 7/1987 | Coates et al. .................... | 358/166 |

OTHER PUBLICATIONS

Langlois, Y. E. et al, "Computer-Based Pattern Recognition of Carotid Artery Doppler Signals for Disease Classification: Prospective Validation", UTS in Med. & Biology, vol. 10, No. 5, pp. 581-595, 1984.

Weissler, A., "Non-Invasive Cardiology", Chapter 6, STI Intervals, pp. 301-368, Grune & Stratton, N.Y., 1974.

Spoto, T. et al, "uP Based Real-Time STI System", Proc. 7th New Eng. (NE) Bioeng. Conf., Troy, N.Y., USA (22–Nov. 23, 1979).

S. Sato, "Ultrasonic Doppler Technique", The Toshiba Medical Review, vol. 10, pp. 1-6 (1983).

H. Monnaka et al., "Analysis of Right and Left Ventricular Systolic Time Intervals in Old Myocardial Infarction by Pulsed Doppler Echocardiography", JSUM Proceedings, Nov. 1985, pp. 249-250.

D. R. Prytherch & D. H. Evans, "Versatile Microcomputer-Based System for the Capture, Storage and Processing of Spectrum-Analyzed Doppler Ultrasound Blood Flow Signals", Medical & Biological Engineering & Computing, Sep. 1985, pp. 445-452.

Primary Examiner—Francis Jaworski
Attorney, Agent, or Firm—Finnegan, Henderson, Farabow, Garrett & Dunner

[57] ABSTRACT

An ultrasonic imaging apparatus has an ultrasonic transducer for radiating ultrasonic beams onto a subject to be examined, and outputs echo waves from the subject, in the form of echo signals. The echo signals are input to a Doppler signal analyzer, and are output as Doppler data. M-mode data obtained by signal-processing the echo signals and ECG and PCG data from an external apparatus are stored in a frame memory to be delayed from the Doppler data by a time corresponding to a time difference therebetween in order to correct the time difference.

9 Claims, 5 Drawing Sheets

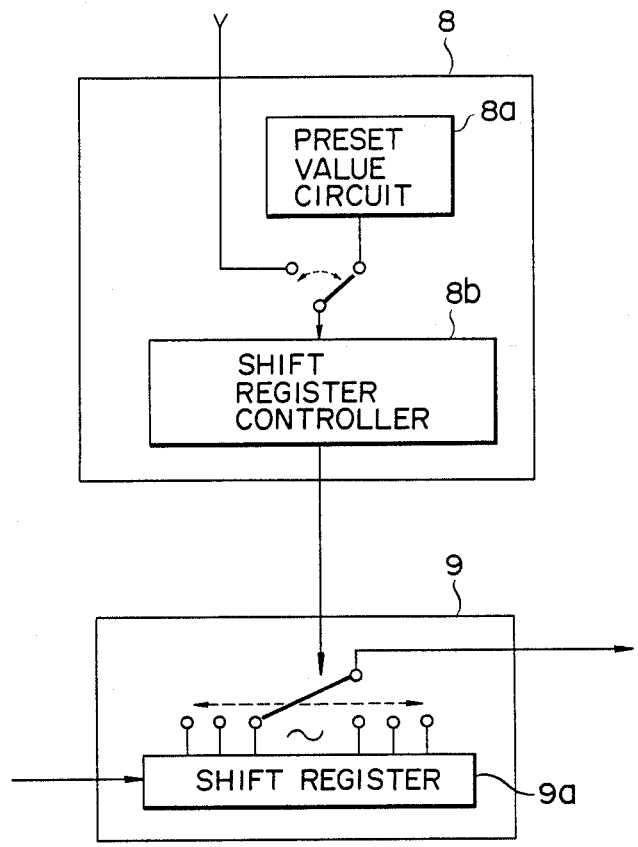
F I G. 3

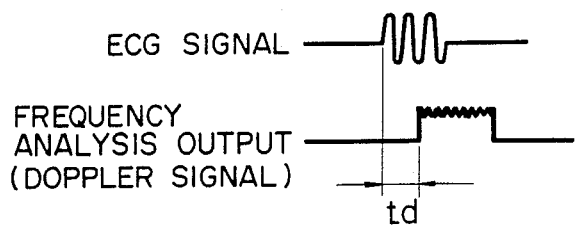
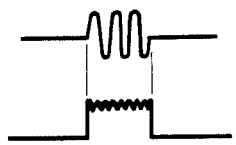
FIG. 4A    FIG. 4B
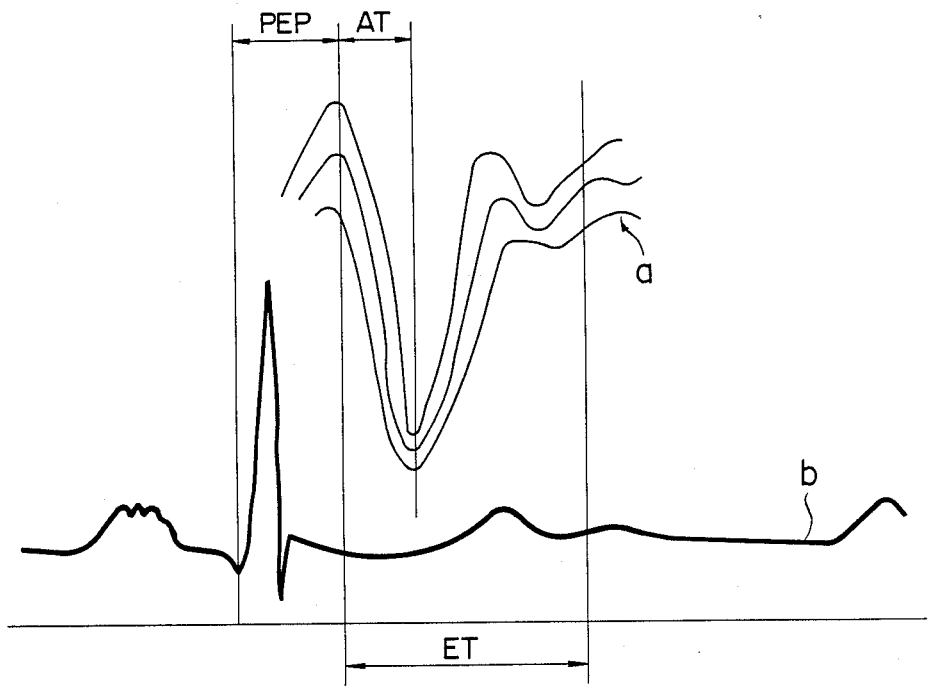
FIG. 5

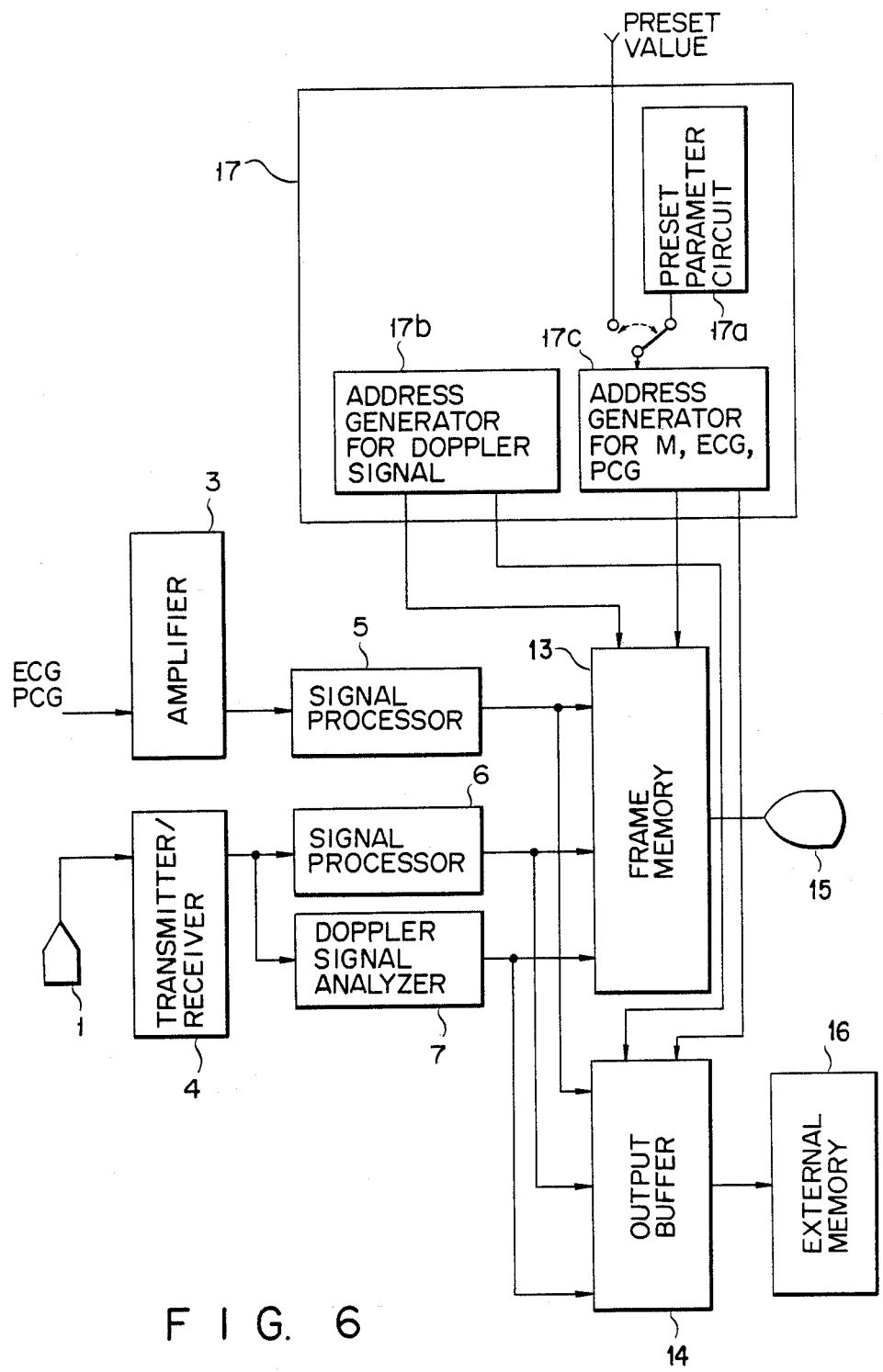
F I G. 6

ULTRASONIC IMAGING APPARATUS

BACKGROUND OF THE INVENTION

The present invention relates to an ultrasonic imaging apparatus which can output Doppler data and M-mode data and/or ECG (Electrocardiograph) and PCG (Phonocardiograph) data together.

An ultrasonic imaging apparatus is widely used particularly in the medical field as an ultrasonic diagnosis apparatus. The ultrasonic diagnosis apparatus has a function of not only displaying a tomographic image, but also displaying ECG and PCG data together with Doppler data to represent blood flow characteristics on a single screen.

When the ECG, PCG, and M-mode image are displayed together with Doppler data pattern, a time from when a valve of the heart is opened until the blood flow starts, i.e., PEP (Pre Ejection Period) can be measured. The cardiac function can be diagnosed in accordance with this measurement value.

However, in order to obtain Doppler data, echo signals obtained from an ultrasonic transducer are subjected to FFT (Fast Fourier Transformation) for frequency analysis.

When the Doppler data is to be obtained by the FFT, the echo signal must be subjected to sampling and arithmetic operations. Therefore, a considerable time is required from when the echo signal is output until the Doppler signal is output. For this reason, the Doppler data output is to be delayed from the M-mode data and the ECG and PCG data. This delay time is included in the PEP, and hence the PEP cannot be accurately measured.

SUMMARY OF THE INVENTION

It is an object of the present invention to provide an ultrasonic imaging apparatus which can output M-mode data and ECG and PCG data together with Doppler data at the same time.

According to the present invention, there is provided an ultrasonic imaging apparatus comprising a means for outputting image data such as M-mode data and ECG and PCG data together with Doppler data at the same time.

BRIEF DESCRIPTION OF THE DRAWINGS

FIG. 3 is a circuit diagram of a timing circuit.

FIGS. 4A and 4B are waveform charts showing Doppler and ECG signals, respectively;

FIG. 5 is a graph showing the Doppler and ECG signals displayed on a monitor display; and FIG. 6 is a block diagram showing an ultrasonic imaging apparatus according to another embodiment of the present invention.

DETAILED DESCRIPTION OF THE PREFERRED EMBODIMENTS

Figure 1:
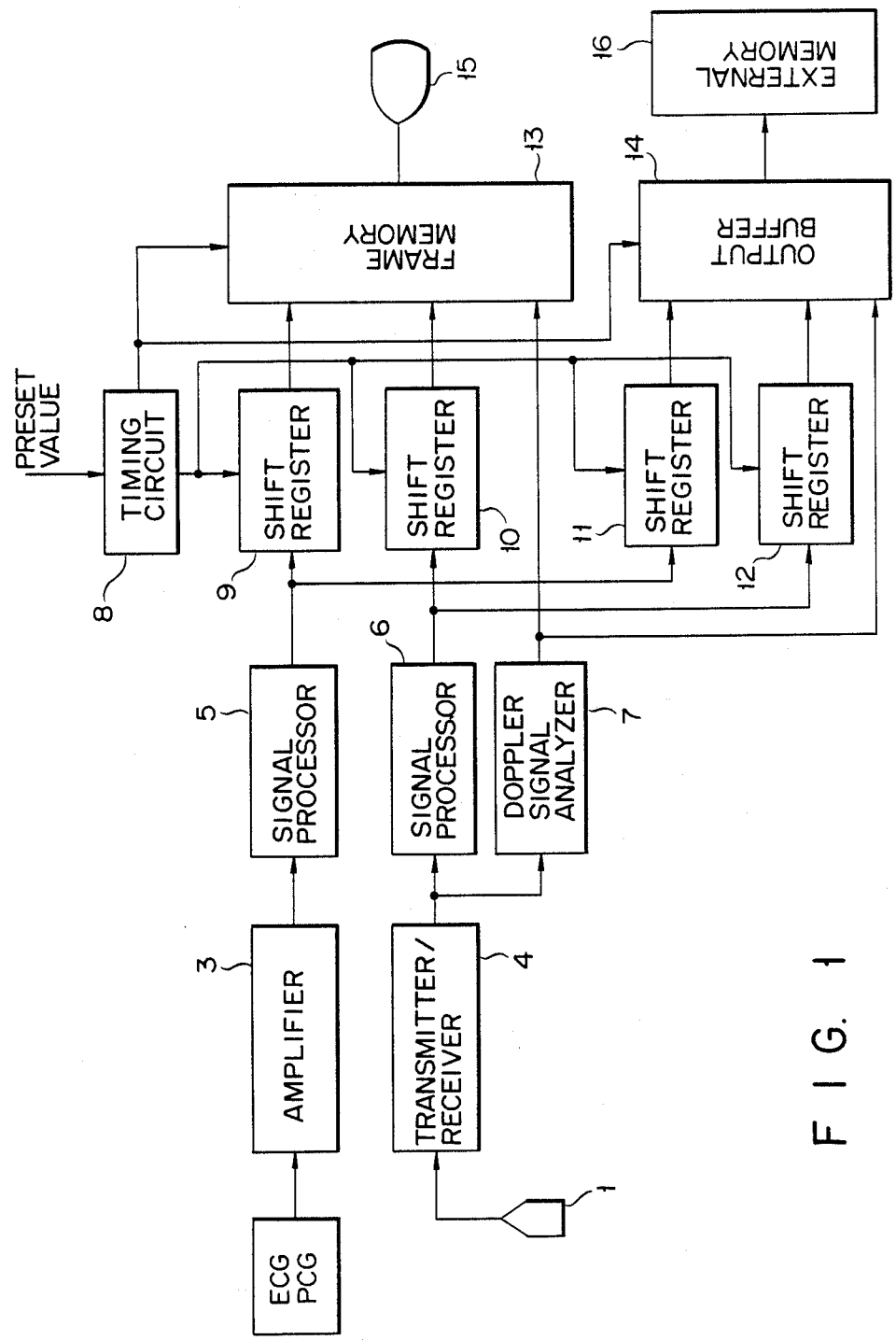
FIG. 1 is a block diagram of an ultrasonic imaging apparatus according to an embodiment of the present invention.

Referring to FIG. 1, ultrasonic transducer 1 is connected to transmitter/receiver 4. Transmitter/receiver 4 comprises a conventional ultrasonic transmission/reception circuit for outputting a drive pulse signal to ultrasonic transducer 1 and for amplifying echo signals from transducer 1. The output terminal of transmitter/receiver circuit 4 is connected to image signal processor 6 and Doppler signal analyzer 7. Image signal processor 6 performs orthogonal detection, sampling, FFT, and the like for the Doppler signal, thereby measuring a Doppler frequency.

The output terminal of an ECG/PCG apparatus is connected to signal processor 5 through amplifier 3. Signal processor 5 filters and samples external signals such as ECG and PCG signals. The output terminals of signal processors 5 and 6 are connected to frame memory 13 respectively through shift register circuits 9 and 10. Frame memory 13 is directly connected to Doppler signal analyzer 7. Output buffer memory 14 is connected to external memory 16.

Shift register circuits 9 to 12, frame memory 13, and output buffer memory 14 are connected to timing circuit 8, which controls read/write access timings of these shift registers and memories.

In the ultrasonic imaging apparatus with the above arrangement, when ultrasonic transducer 1 is driven by the drive pulse signal from transmitter/receiver 4, it radiates ultrasonic beams onto subject to be examined (patient). Echo waves from the patient are converted to echo signals by ultrasonic transducer 1, and are amplified by transmitter/receiver 4. The echo signal output from transmitter/receiver 4 is signal-processes by signal processor 6, and is input to shift register 10 as an image signal.

The echo signal input to Doppler signal analyzer 7 is signal-processed thereby in order to obtain Doppler data. More specifically, Doppler signal analyzer 7 performs data collection (sampling), FFT processing, Doppler signal transfer, and the like, and outputs Doppler data. A delay time corresponding to a time (about 20 msec) is required for sampling 64 or 128 points and processing the sampling data is generated until Doppler data is output after the echo signal is input to Doppler signal analyzer 7. Therefore, a delay time is present between M-mode signals from signal processor 6 and the Doppler data from Doppler signal analyzer 7. In order to compensate for this delay time, M-mode data stored in shift register circuit 10 are read out at a timing corresponding to the delay time (20 msec), and are transferred to frame memory 13. Therefore, the M-mode data and the Doppler data can be simultaneously stored in frame memory 13.

Figure 2:
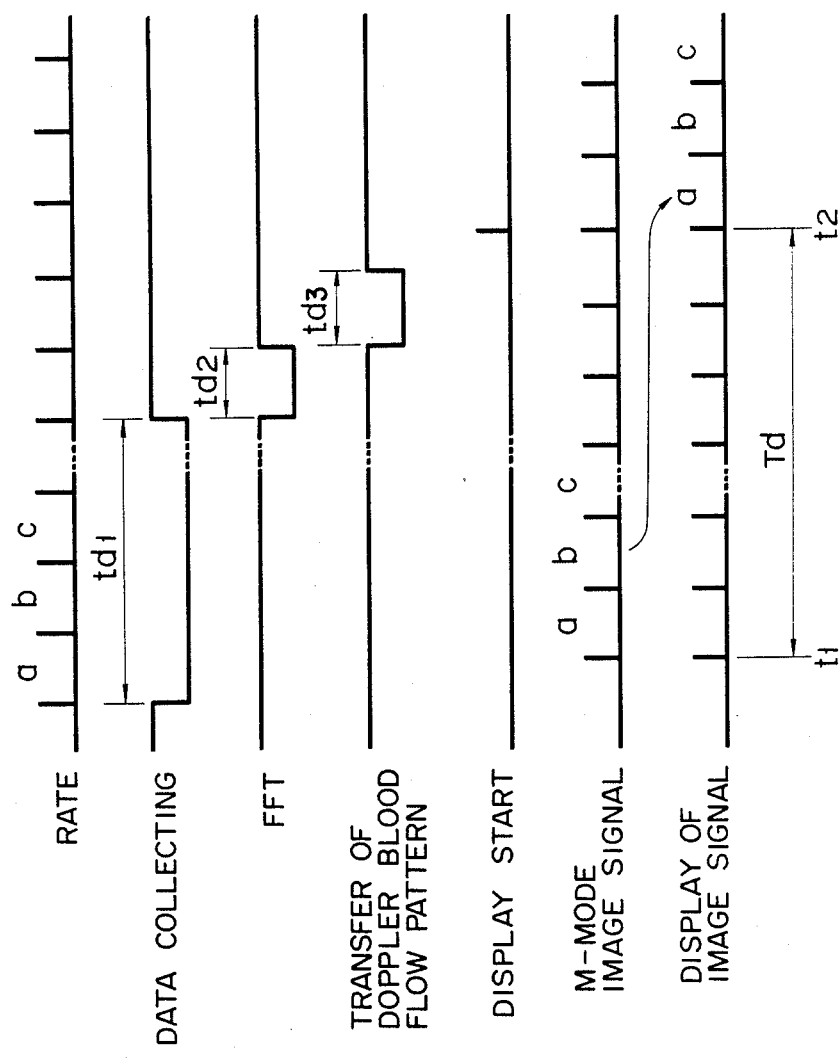
FIG. 2 is a timing chart for explaining the operation of the apparatus shown in FIG. 1.

The above-mentioned operation will now be described with reference to the timing chart shown in FIG. 2 M-mode data are output from signal processor 6 as data a, b, c, ... in synchronism with rate signals, and are sequentially stored in shift register circuit 10 from time t1.

The Doppler data is output from time t2 delayed from time t1 by a time including a data collection time, an FFT processing time, and a Doppler data transfer time, i.e., by time Td. The Doppler data is input to frame memory 13 and is stored therein. In this case, the M-mode data stored in shift register 10 are sequentially read out therefrom in the order of a, b, c,..., and are stored in frame memory 13. Therefore, the M-mode data and the Doppler data are stored in frame memory 13 at the same time.

The M-mode data and the Doppler data stored in frame memory 13 are read out together therefrom, and are input to display 15. Thus, the M-mode image and a Doppler blood flow pattern are displayed on display 15 at the same time.

Delay time Td is calculated from data acquisition time td1, frequency analysis time td2, and transfer time td3, or is obtained by measurement. Data corresponding to delay time Td is stored in present value circuit 8a shown in FIG. 3. When the present data (Td) is input to a shift register controller 8b, shift register 9a of the shift register circuit 9 is preset at the valve Td by shift register controller 8b. Shift register circuit 9 can be preset by the preset data from an external circuit through shift register controller 8b.

When ECG and PCG signals are input form an external apparatus, e.g., the ECG/PCG apparatus to amplifier 3, these signals are amplified by amplifier 3, and are then input to signal processor 5. The ECG and PCG signals signal-processed by signal processor 5 are output at an earlier timing from that of the Doppler signal by time Td in the same manner as the M-mode signals, as shown in FIG. 4A. The ECG and PCG signals are stored in shift register circuit 9 from time t1, are read out from time t2, and are then transferred to frame memory 13. At this time, ECG, PCG, and Doppler data are stored in frame memory 13 at the same time, as shown in FIG. 4B.

The ECG, PCG, and Doppler data are read out from frame memory 13 and are input to display 15. As shown in FIG. 5, Doppler blood flow pattern (a) and ECG (PCG) pattern (b) are displayed on display 15. Since Doppler blood flow pattern (a) and ECG pattern (b) are displayed at the same timing, PEP, AT (Acceleration Time) and ET (Ejection Time) data are measured from these patterns, thereby diagnosing the conditions of the heart.

When the ECG and PCG data, or M-mode data are stored in external memory 16 together with the Doppler data, ECG and PCG data are temporarily stored in shift register circuit 11 and M-mode data are temporarily stored in shift register circuit 12 and are a read out from shift register circuits 11 and 12 at a time coinciding with an output time of the Doppler data to be stored in output buffer memory 14. When the ECG and PCG data or M-mode data, and the Doppler data are transferred from output buffer memory 14 to external memory 16, they can be stored in memory 16 at the same time.

In the above embodiment, the data read timing of shift register circuits 9 to 12 and data write timing of frame memory 13 are determined by a timing signal from timing circuit 8. For this purpose, preset value circuit 8a comprises a preset counter, and is preset to have a calculated value or measurement value of delay time Td. Timing circuit 8 generates a timing signal delayed from the rate pulse by time Td. The preset value can be automatically set. In this case, a time difference between the Doppler signal and other signals is counted by, e.g., a counter in response to the leading or trailing edges of the signals, and the count value is preset in timing circuit 8.

In an embodiment shown in FIG. 6, signal processors 5 and 6 and Doppler signal analyzer 7 are directly connected to frame memory 13 and output buffer memory 14. Write timings of memories 13 and 14 are determined by write address generator 17. More specifically, when Doppler data is input to memories 13 and 14 to be delayed by time Td, write address generator 17b sends to memories 13 and 14 a smaller address than a write address of other data (e.g., ECG data) by the number of pixels corresponding to time difference Td (td). For example, assuming that the Doppler data is output to be delayed by a time corresponding to 10 pixels, when ECG data is stored at address "10" by the address data from address generator 17c, the Doppler data is stored at address "1" by the address data from address generator 17b. Thus, the time difference between the Doppler data and the ECG data can be corrected, and these data can be stored in memories 13 and 14 at the same time.

The Doppler data and other data stored in frame memory 13, as described above, are read out and input to display 15. Thus, a Doppler blood flow pattern, and a pattern represented by other data can be displayed on display 15 at the same time.

According to the present invention, even if Doppler data is output to be delayed from other data, e.g., M-mode data and ECG and PCG data, the Doppler data can be displayed on a display or stored in a memory without providing a time difference therebetween, and this is particularly effective for cardiac diagnosis.

What is claimed is:

1. An ultrasonic imaging apparatus comprising:

ultrasonic transducer means for radiating ultrasonic beams onto a subject to be examined, the subject containing a fluid flowing at a velocity, and for converting echoes of said ultrasonic beams from the subject to be examined into an echo signal;

signal-processing means coupled to said ultrasonic transducer means, for signal-processing the echo signal from said ultrasonic transducer means, and for generating at a first time Doppler data corresponding to the velocity of the fluid during a specific time, said Doppler data being generated a predetermined delay time after the specific time;

means for generating examination data corresponding to a parameter of the subject other than flow velocity during the specific time, said examination data being generated at a second time prior to said first time;

time difference correcting means for correcting a time difference between the first time and the second time by simultaneously outputting Doppler data generated at the first time and examination data generated at the second time; and display means for visually presenting the examination data and the Doppler data output by said time difference correcting means;

wherein said time difference correcting means comprises storage means for temporarily storing the examination data, means for reading out examination data from said temporary storage means after the delay time to simultaneously output Doppler data generated at the first time and examination data generated at the second time, and frame memory means coupled to the display means for storing the examination data read out from said temporary storage means and the Doppler data.

2. An apparatus according to claim 1, wherein said examination data generating means comprises an electrocardiograph (ECG) device for generating electrocardiograph (ECG) data relating to a patient.

3. An apparatus according to claim 1, wherein said examination data generating means comprises means for signal-processing the echo signal and generating M-mode data corresponding to M-mode images relating to a patient.

4. An apparatus according to claim 1, wherein said examination data generating means comprises a phonocardiograph (PCG) device for generating phonocardiograph (PCG) data relating to a patient.

5. An apparatus according to claim 1, wherein said display means comprises means for displaying the examination data and the Doppler data together at the same time.

6. An apparatus according to claim 5, wherein said examination data generating means comprises means for signal-processing the echo signal and for generating M-mode data, and said display means comprises means for displaying the M-mode data as M-mode images.

7. An apparatus according to claim 5, wherein said examination data generating means comprises at least one of an ECG device and a PCG device for generating at least one of ECG data and PCG data relating to a patient, and said display means comprises means for displaying at least one of the ECG data and PCG data as ECG and PCG patterns.

8. An ultrasonic imaging apparatus comprising:
ultrasonic transducer means for radiating ultrasonic beams onto a subject to be examined, the subject containing a fluid flowing at a velocity, and for converting echoes of said ultrasonic beams from the subject to be examined into an echo signal;
signal-processing means coupled to said ultrasonic transducer means, for signal-processing the echo signal from said ultrasonic transducer means, and for generating at a first time Doppler data corresponding to the velocity of the fluid during a specific time, said Doppler data being generated a predetermined delay time after the specific time;
means for generating examination data corresponding to a parameter of the subject other than flow velocity during the specific time, said examination data being generated at a second time prior to said first time;
time difference correcting means for correcting a time difference between the first time and the second time by simultaneously outputting Doppler data generated at the first time and examination data generated at the second time; and
display means for visually presenting the examination data and the Doppler data output by said time difference correcting means;
wherein said time difference correcting means comprises frame memory means coupled to the display means for storing the examination data and the Doppler data, and means for selecting a write address at which the Doppler data is stored in said frame memory means to accelerate the output of the Doppler data by said frame memory means, wherein Doppler data generated at the first time and examination data generated at the second time are simultaneously output by the frame memory means.

9. An apparatus according to claim 8, wherein said examination data generating means comprises at least one of an ECG device and a PCG device for generating at least one of ECG data and PCG data relating to a patient.

* * * * *